United States Patent [19]
Alexander et al.

[11] Patent Number: 5,720,727
[45] Date of Patent: Feb. 24, 1998

[54] SAFETY SYRINGE

[75] Inventors: Gary E. Alexander, Baton Rouge, La.; Thomas Wade Fallin, Hyde Park, Utah

[73] Assignee: Medisys Technologies, Inc., Baton Rouge, La.

[21] Appl. No.: 727,756

[22] Filed: Oct. 8, 1996

Related U.S. Application Data

[63] Continuation-in-part of Ser. No. 301,541, filed as PCT/US95/11426, Sep. 6, 1994, Pat. No. 5,460,611.

[51] Int. Cl.$^6$ .................................................. A61M 5/00
[52] U.S. Cl. .................. 604/110; 604/192; 604/198
[58] Field of Search ........................ 604/198, 263, 604/187, 164–170, 53, 192

[56] References Cited

U.S. PATENT DOCUMENTS

| | | | |
|---|---|---|---|
| 3,094,122 | 6/1963 | Gauthier et al. | 604/164 |
| 4,026,287 | 5/1977 | Haller | 128/215 |
| 4,197,846 | 4/1980 | Bucalo | 128/218 |
| 4,425,120 | 1/1984 | Sampson | 604/198 |
| 4,464,171 | 8/1984 | Garwin | 604/164 X |
| 4,581,021 | 4/1986 | Landau et al. | 604/212 |
| 4,636,202 | 1/1987 | Lowin et al. | 604/236 |
| 4,702,738 | 10/1987 | Spencer | 604/198 |
| 4,737,150 | 4/1988 | Baeumle et al. | 604/198 |
| 4,846,785 | 7/1989 | Cassou et al. | 600/34 |
| 4,846,799 | 7/1989 | Tanaka et al. | 604/158 |
| 4,850,996 | 7/1989 | Cree | 604/198 |
| 4,863,434 | 9/1989 | Bayless | 604/198 |
| 4,863,435 | 9/1989 | Sturman et al. | 604/198 |
| 4,874,382 | 10/1989 | Lindemann et al. | 604/195 |
| 4,875,896 | 10/1989 | Kurtz | 604/187 |
| 4,883,471 | 11/1989 | Michel | 604/195 |
| 4,883,472 | 11/1989 | Michel | 604/208 |
| 4,892,107 | 1/1990 | Haber | 128/763 |
| 4,894,055 | 1/1990 | Sudnak | 604/198 |
| 4,909,791 | 3/1990 | Norelli | 604/192 |
| 4,909,792 | 3/1990 | Norelli | 604/192 |
| 4,923,445 | 5/1990 | Ryan | 604/195 |
| 4,929,237 | 5/1990 | Medway | 604/198 |
| 4,935,014 | 6/1990 | Haber | 604/195 |
| 4,935,016 | 6/1990 | DeLeo | 604/198 |
| 4,936,830 | 6/1990 | Verlier | 604/110 |
| 4,944,723 | 7/1990 | Haber et al. | 604/110 |
| 4,966,592 | 10/1990 | Burns et al. | 604/198 |
| 4,966,593 | 10/1990 | Lennox | 604/198 |
| 4,969,877 | 11/1990 | Kornberg | 604/195 |
| 4,973,316 | 11/1990 | Dysarz | 604/195 |
| 4,973,317 | 11/1990 | Bobrove | 604/198 |
| 4,976,701 | 12/1990 | Ejlersen et al. | 604/192 |
| 4,982,842 | 1/1991 | Hollister | 604/198 |
| 4,986,819 | 1/1991 | Sobel | 604/198 |
| 4,994,041 | 2/1991 | Dombrowski et al. | 604/198 X |
| 5,015,240 | 5/1991 | Soproni et al. | 604/192 |
| 5,026,353 | 6/1991 | Bartman | 604/192 |
| 5,032,117 | 7/1991 | Motta | 604/88 |
| 5,051,109 | 9/1991 | Simon | 604/263 |
| 5,067,942 | 11/1991 | Jaffe et al. | 604/110 |
| 5,092,851 | 3/1992 | Ragner | 604/192 |
| 5,092,852 | 3/1992 | Poling | 604/192 |
| 5,098,401 | 3/1992 | De Lange | 604/192 |
| 5,104,384 | 4/1992 | Parry | 604/192 |
| 5,122,123 | 6/1992 | Vaillancourt | 604/192 |
| 5,135,507 | 8/1992 | Haber et al. | 604/187 |
| 5,151,088 | 9/1992 | Allison | 604/192 |
| 5,205,825 | 4/1993 | Allison et al. | 604/110 |
| 5,282,792 | 2/1994 | Imbert | 604/187 |
| 5,300,038 | 4/1994 | Haber et al. | 604/187 |
| 5,306,258 | 4/1994 | de la Fuente | 604/198 |
| 5,314,503 | 5/1994 | Bobrove et al. | 604/263 X |
| 5,342,320 | 8/1994 | Cameron | 604/192 |
| 5,370,628 | 12/1994 | Allison et al. | 604/192 |
| 5,385,555 | 1/1995 | Hausser | 604/192 |

FOREIGN PATENT DOCUMENTS 65-08468  3/1989  Japan.

*Primary Examiner*—John D. Yasko
*Attorney, Agent, or Firm*—Roy, Kiesel & Tucker, PLC

[57] ABSTRACT

A safety syringe is disclosed and claimed. The safety syringe has a hollow barrel and a plunger. The plunger enters the barrel from one end and a needle leaves the barrel from the other end. A thin blunt sheath is positioned over the needle. The sheath has an exposed position in which the point of the needle is exposed and a covered position in which the point of the needle is covered. A connector functionally joins the sheath to the plunger so that the sheath is advanced from the exposed position to the covered position as the plunger is advanced. In operation, the safety syringe is filled like a conventional syringe by placing the needle in a vial of medication and drawing back on the plunger. Once the safety syringe is filled, the needle is inserted into the patient. The needle should be inserted a sufficient distance to insert the end of the sheath into the patient as well. The medication is then injected into the patient by depressing the plunger. Depressing the plunger will, as stated, advance the sheath from the exposed position to the covered position. Thus, the needle may be covered before it is removed from the patient.

38 Claims, 5 Drawing Sheets

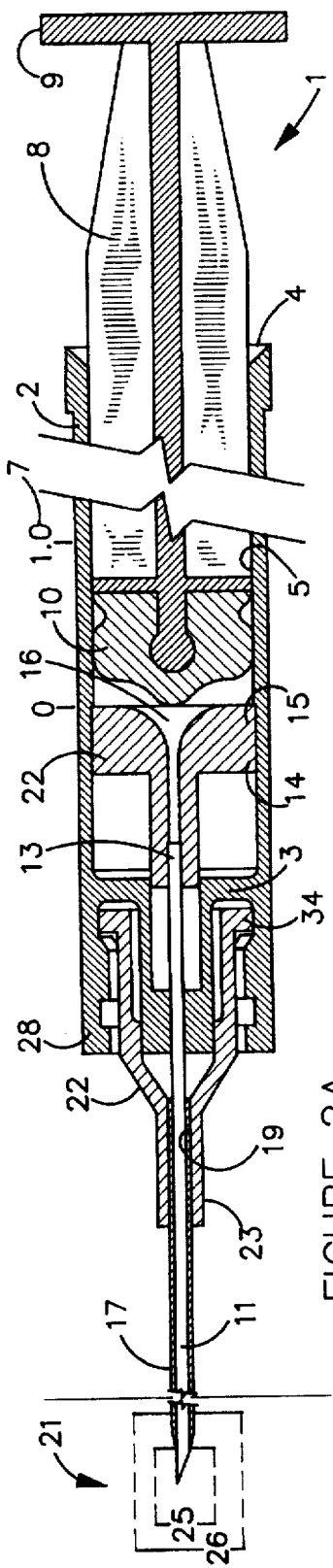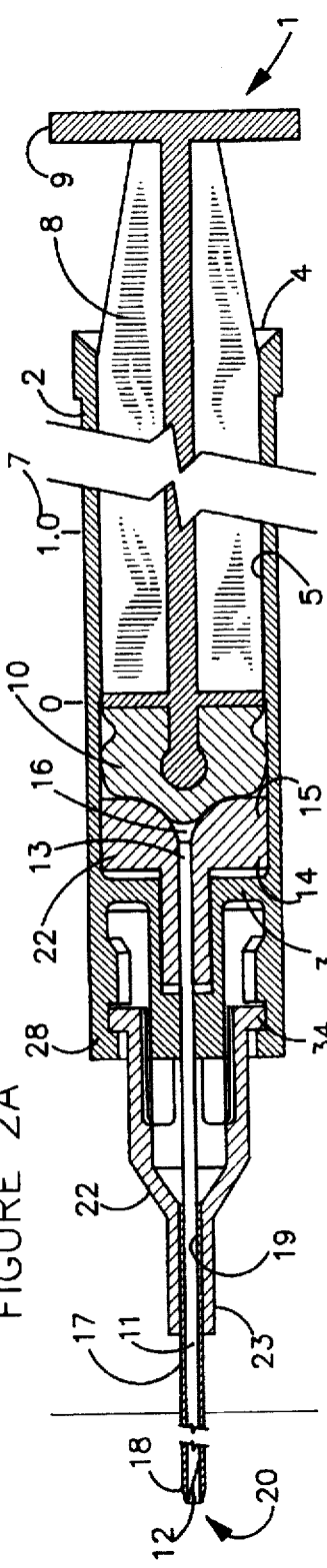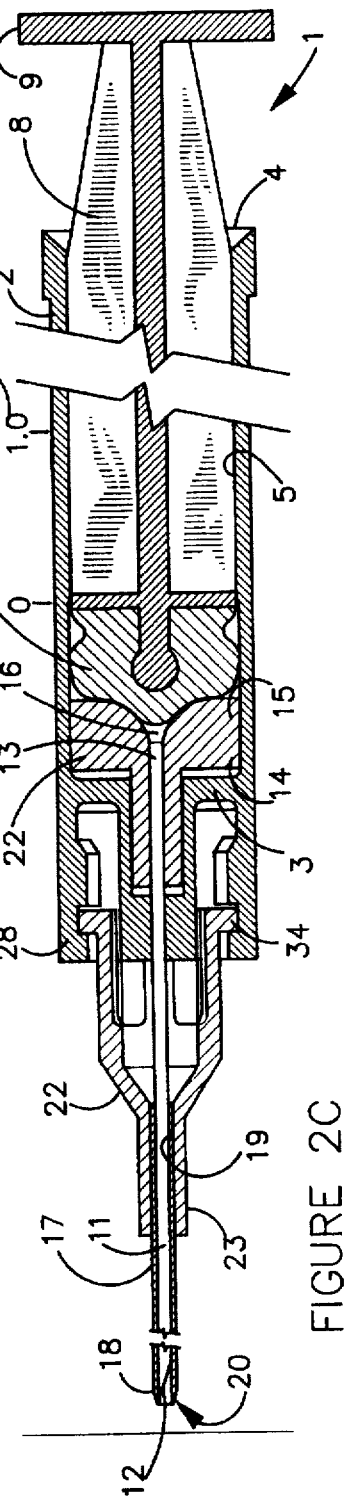

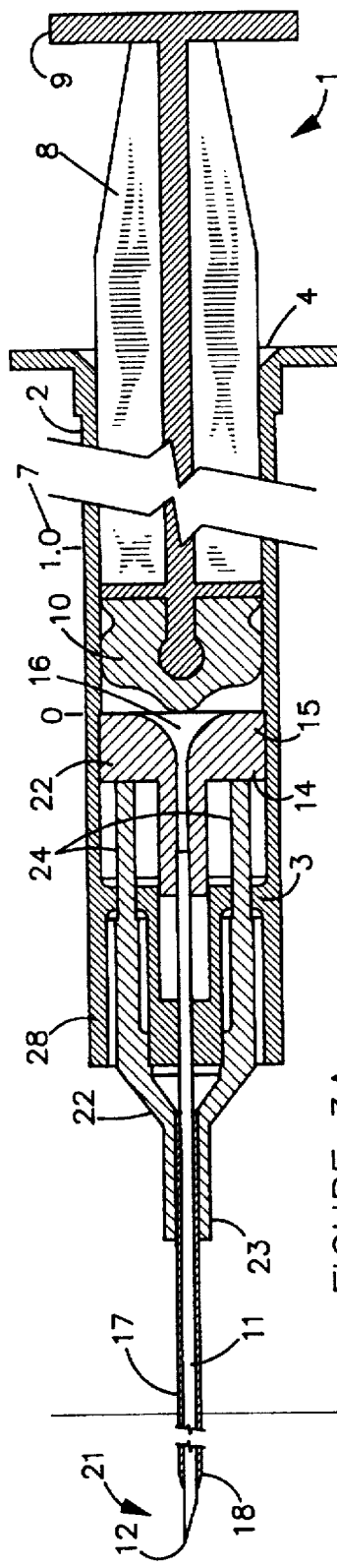
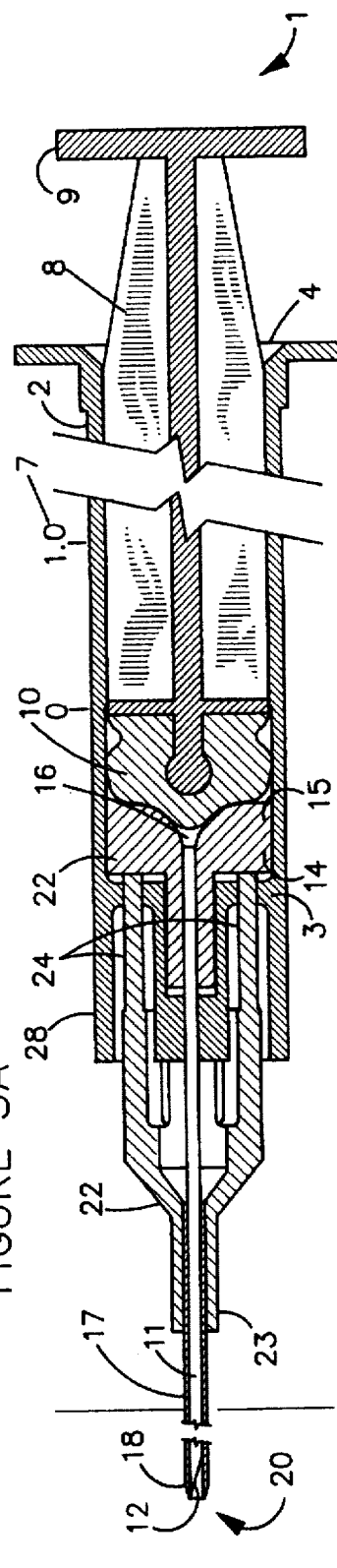
FIGURE 3A  FIGURE 3B  FIGURE 3C

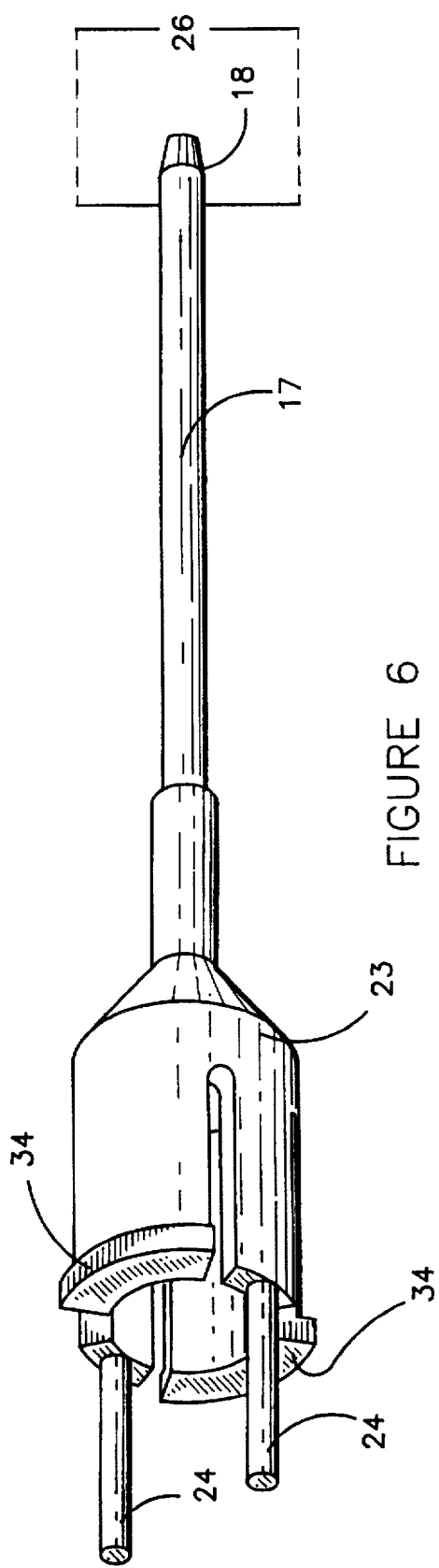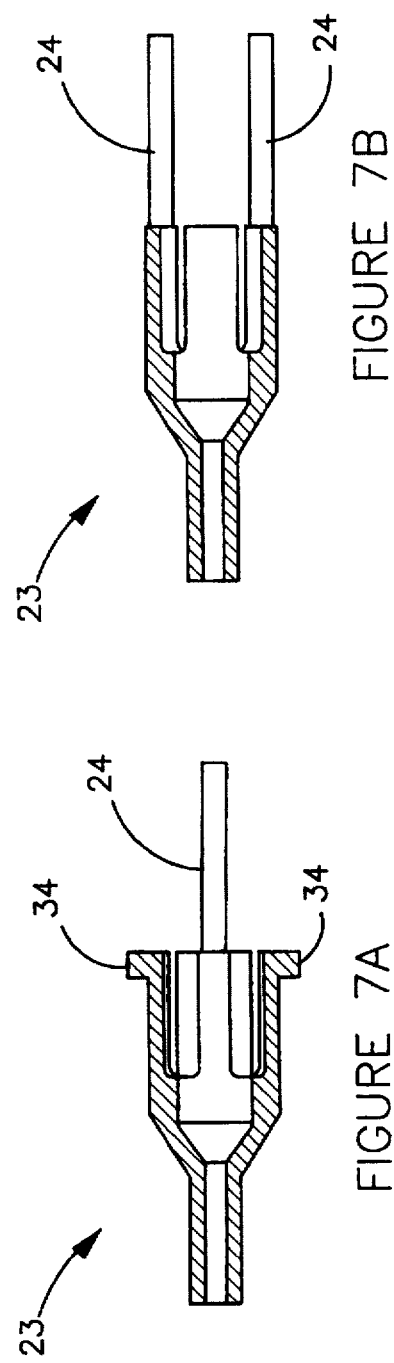

SAFETY SYRINGE

This is a continuation-in-part of PCT application number PCT/US95/11426 which is a continuation-in-part of U.S. application number 08/301,541, now U.S. Pat. No. 5,460,611, both of which are hereby incorporated by reference in their entirety.

BACKGROUND OF THE INVENTION

1. Field of the Invention

The invention relates generally to hypodermic syringes and particularly to safety syringes designed to avoid accidental sticks.

2. Prior Art

The risk of contracting diseases such as HIV or hepatitis from accidental sticks with dirty needles is a potentially deadly hazard for medical professionals. Many syringe designs have been created that attempt to avoid or minimize this risk. Such syringes generally have three typical goals. They should minimize the window of opportunity for an accidental stick. They should be simple to operate and preferably operate as similarly as possible to a conventional syringe. They should also be easy to manufacture. The prior art known to the inventor is lacking a safety syringe which adequately addresses all of these goals. Therefore, a safety syringe meeting the following objectives is desired.

OBJECTS OF THE INVENTION

It is an object of the invention to provide a safety syringe that minimizes the window of opportunity for an accidental stick.

It is an object of the invention to provide a safety syringe that automatically covers the needle upon the administration of the injection.

It is a another object of the invention to provide a safety syringe that can cover the needle prior to its removal from the patient.

It is another object of the invention to provide a safety syringe that can be operated with one hand.

It is another object of the invention to provide a safety syringe that can be used like a conventional syringe.

It is yet another object of the invention to provide a safety syringe that can be used to draw up medications and to purge air from the syringe.

It is still another object of the invention to provide a safety syringe that is relatively easy and inexpensive to manufacture and that is simple in operation.

These and other objects and advantages of the invention shall become obvious from the figures and from the following descriptions of the preferred embodiments of the invention.

SUMMARY OF THE INVENTION

A safety syringe is disclosed. The safety syringe is comprised of an elongated hollow barrel having a needle end and an open end. A plunger is insertable into the open end of the barrel. The end of the plunger is fitted to the inside of the barrel so that it creates a fluid tight seal between it and the interior wall of the barrel. A needle extends from the needle end of the barrel. One end of the needle is contained within the barrel while the sharp end is external to the barrel so that the needle provides a fluid passage from the interior of the barrel to its exterior. Thus the contents of the syringe may be evacuated through the needle by depressing the plunger. By inserting the needle into the desired object and depressing the plunger, the contents of the needle may be injected into that object.

A hollow sheath having a tip end and a barrel end is slidably disposed over the needle. The sheath has an exposed position where the point of the needle is exposed and a covered position where the point of the needle is covered. The sheath is functionally connected to the plunger so that the sheath is advanced from the exposed position to the covered position as the plunger is depressed.

The sheath is relatively thin. It should be thin enough that it may be inserted with the needle into the patient when an injection is given, in much the same way as a catheter is inserted. In a preferred embodiment, the sheath should have an external diameter at the tip end of between about 110% and 150% of the external diameter of the needle. After the injection is completed, but prior to the removal of the needle from the patient, the sheath may be advanced into the covered position. Alternatively, the safety syringe may be designed so that the sheath is advanced into the covered position prior to or during the administration of the injection. In any event, the needle can be covered prior to its removal from the patient. Thus, after the injection, there is never a contaminated sharp needle exposed, and the possibility for accidental sticks is greatly reduced.

BRIEF DESCRIPTION OF THE FIGURES

FIG. 2A is a cross-sectional view of a preferred embodiment of the safety syringe during injection.

FIG. 2B is a cross-sectional view of a preferred embodiment of the safety syringe after injection.

FIG. 2C is a cross-sectional view of a preferred embodiment of the safety syringe after injection after having been removed from the patient.

FIG. 3A depicts the preferred embodiment of FIG. 2A rotated 90° about its longitudinal axis.

FIG. 3B depicts the preferred embodiment of FIG. 2B rotated 90° about its longitudinal axis.

FIG. 3C depicts the preferred embodiment of FIG. 2C rotated 90° about its longitudinal axis.

FIG. 6 is a perspective view of a preferred embodiment of the connector and sheath.

FIG. 7A is a cross-sectional view of a preferred embodiment of the connector. FIG. 7B is a cross-sectional view of a preferred embodiment of the connector rotated 90° from the view shown in FIG. 6A.

DETAILED DESCRIPTION OF THE PREFERRED EMBODIMENTS OF THE INVENTION

Figure 1A:
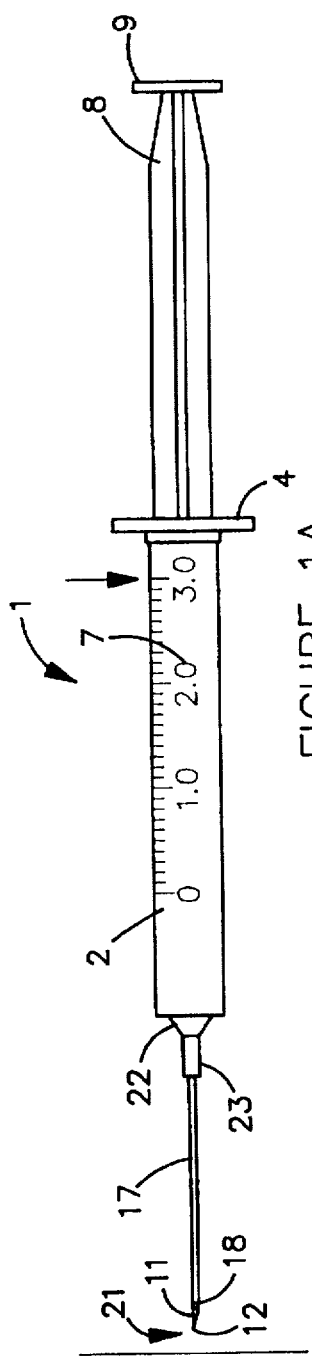
FIG. 1A is a side view of a preferred embodiment of the safety syringe prior to injection.
Figure 1B:
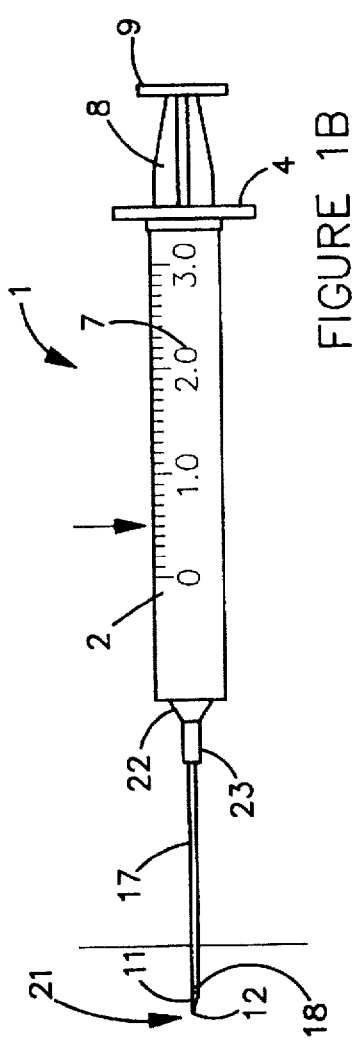
FIG. 1B is a side view of a preferred embodiment of the safety syringe during injection.
Figure 1C:
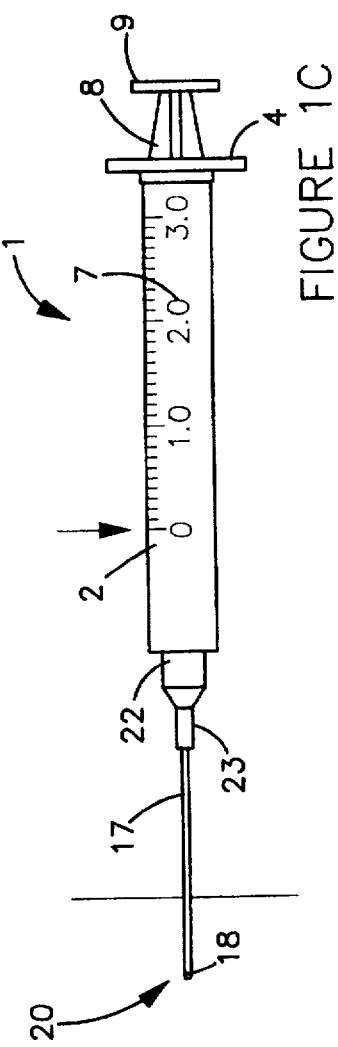
FIG. 1C is a side view of a preferred embodiment of the safety syringe after injection. The arrows shown in FIGS. 1A–1C show the location of the washer end of the plunger.
Figure 4A:
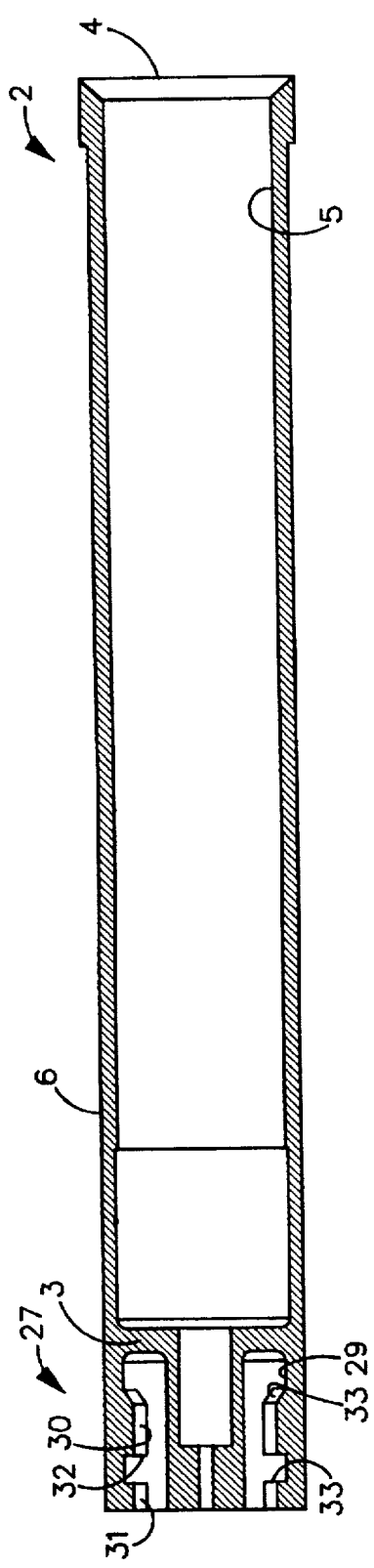
FIG. 4A is a cross-sectional view of a preferred embodiment of the barrel containing the locking housing.
Figure 4B:
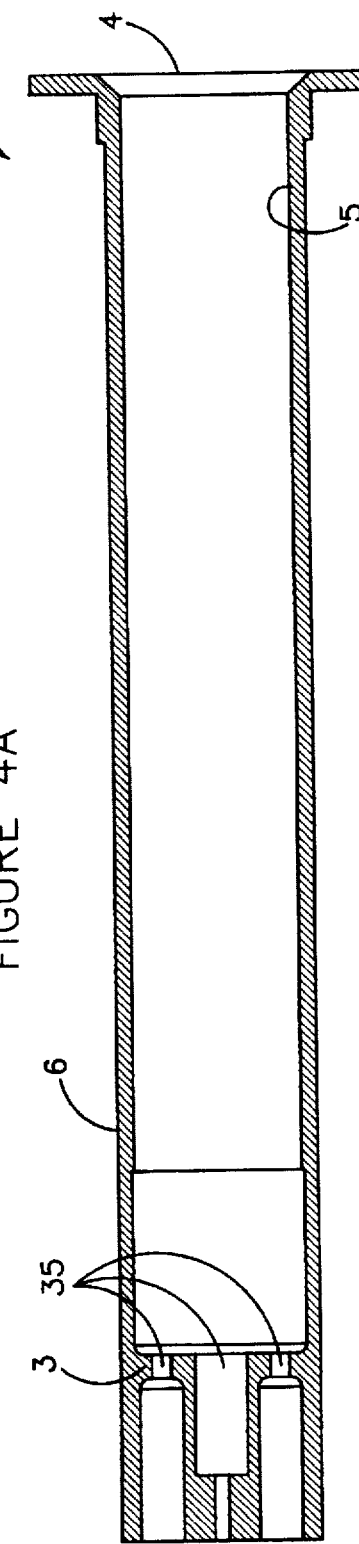
FIG. 4B depicts the preferred embodiment of FIG. 4A rotated 90°.
Figure 5:
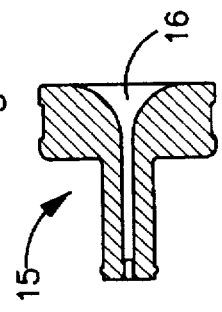
FIG. 5 is a cross-sectional view of a preferred embodiment of the diaphragm.

A safety syringe 1 is disclosed. Safety syringe 1 comprises a substantially hollow barrel 2 having a needle end 3, an open plunger end 4, an interior wall 5, and an exterior wall 6. Needle end 3, plunger end 4 and interior wall 5 define a fluid receiving cavity within barrel 2. In a preferred embodiment, calibrated measurement lines 7 are marked on exterior wall 6. In a preferred embodiment, barrel 2 is made of transparent or translucent plastic.

A plunger 8 fits within barrel 2. Plunger 8 has a thumb end 9 and a washer end 10. Washer end 10 is sized to engage interior wall 5 of barrel 2 so that a substantially fluid tight seal is created between washer end 10 and interior wall 5. In a preferred embodiment, washer end 10 is made of or covered with rubber while plunger 8 is made of plastic. Upon insertion of plunger 8 into barrel 2, the volume of the fluid receiving cavity may be varied by operation of plunger 8.

A hollow needle 11 having a pointed end 12 and a barrel end 13 extends from needle end 3 of barrel 2. Barrel end 13 of needle 11 is positioned within barrel 2 and pointed end 12 is positioned external of barrel 2. Thus, needle 11 provides fluid passage into and out of barrel 13.

In a preferred embodiment, barrel 2 contains a means 14 for creating a substantially fluid tight seal between barrel end 13 of needle 11 and interior wall 5 and needle end 3 of barrel 2. In a preferred embodiment, sealing means 14 comprises a diaphragm 15 slidably positioned over barrel end 13 of needle 11. Diaphragm 15 should be sized to engage interior wall 5 of barrel 2 so that a substantially fluid tight seal is created between diaphragm 15 and interior wall 5. Diaphragm 15 contains an aperture 16 which provides fluid passage through diaphragm 15 and into needle 11. In a preferred embodiment, diaphragm 15 is made of rubber. It should be noted that diaphragm 15 may simultaneously form part of both sealing means 14 and sheath moving means 22, discussed below.

A hollow sheath 17 having a tip end 18 and a barrel end 19 is circumferentially positioned over needle 11. Tip end 18 should not be sharp so that sheath 17 can perform its primary function of preventing accidental sticks with needle 11. In a preferred embodiment tip end 18 may be tapered. Sheath 17 has a covered position 20 in which pointed end 12 of needle 11 is contained within sheath 17. Sheath 17 also has an exposed position 21 in which at least pointed end 12 of needle 11 protrudes from sheath 17. In one alternate embodiment sheath 17 may be fluidly connected to the fluid receiving cavity so that sheath 17 provides passage into and out of the fluid receiving cavity rather than or in conjunction with needle 11. This embodiment is expected to be particularly useful when needle 11 is not hollow.

Safety syringe 1 is equipped with a means 22 for moving sheath 17 from exposed position 21 to covered position 20. In one embodiment, sheath moving means 22 may comprise a push tab attached to sheath 17 to allow sheath 17 to be pushed forward into covered position 20. In another preferred embodiment, sheath moving means may comprise a hydraulic cylinder actuated by the motion of fluid within barrel 2 ahead of advancing plunger 8. In another preferred embodiment, sheath moving means 22 comprises a connect 23. Connector 23 is fixably attached to sheath 17 and is positioned to functionally engage plunger 8 as plunger 8 is moved from open end 4 to needle end 3 of barrel 2. When connector 23 is so engaged, sheath 17 will move from exposed position 21 to covered position 20 as plunger 8 moves toward needle end 3.

Connector 23 may engage plunger 8 in several ways. In one preferred embodiment, connector 23 comprises at least one pushrod 24. Pushrod 24 extends through needle end 3 of barrel 2 and contacts diaphragm 15. When washer end 10 of plunger 8 engages diaphragm 15, further pressure on plunger 8 will cause diaphragm 15 to move forward, which in turn will cause pushrod 24 and connector 23 to move forward. In another embodiment, diaphragm 15 may be omitted. In that embodiment, pushrod 24 will extend through needle end 3, and washer end 10 of plunger 8 will contact pushrod 24 directly, rather than through diaphragm 15. In this embodiment, the holes 35 in needle end 3 of barrel 2 through which pushrod 24 and needle 11 pass should be substantially fluid tight when pushrod 24 and needle 11 are in place in order to prevent leakage of the contents of safety syringe 1.

It should be recognized that a myriad of other equivalent sheath moving means 22 are possible which should be obvious to those skilled in the art in view of the foregoing description.

Needle 11 will have an external diameter 25. Likewise, sheath 17 will have an external diameter 26. While preferred embodiments of both needle 11 and sheath 17 are generally cylindrical, it is recognized that both may have other shapes such that their cross section is not a circle. In such cases, diameter is intended herein to refer to the longest cross sectional dimension of the respective article unless otherwise indicated. External diameter 26 of sheath 17 at tip end 18 should be close enough to external diameter 25 of needle 11 to allow tip end 18 of sheath 17 to be inserted with needle 11 when safety syringe 1 is used to administer an injection. As needle 11 is inserted into tissue, it will create a puncture wound or tear in that tissue that is somewhat larger in diameter than external diameter 25 of needle 11. Sheath 17, and particularly tip end 18 should be sized to permit at least tip end 18 of said sheath 17 to be inserted simultaneously with needle 11 into the puncture wound created by needle 11 during hypodermic injection.

In designing sheath 17, there are two competing goals, strength or puncture resistance and patient comfort. The thinner sheath 17 is, the more comfortable it will be for the patient when sheath 17 is inserted with needle 11 during injection. However, as sheath 17 is made thinner, it becomes less resistant to punctures and thus less able to perform its task of preventing accidental sticks. Therefore, a balance must be struck between these two competing goals when sheath 17 is designed. Of course, where this balance will fall will depend upon the characteristics of the materials used to make sheath 17. Currently, the inventors contemplate using plastic, Teflon®, or a metal such as braided stainless steel. However, other acceptable rigid or semi-rigid substances may be available now or developed in the future which may affect the thickness of sheath 17. Furthermore, it is anticipated that a non-rigid substance such as soft rubber which relies on needle 11 for its rigidity during insertion would perform adequately as a substance from which sheath 17 might be constructed.

The thickness of sheath 17 will also vary with the size of needle 11. Needles come twenty five standard gauges, where gauge is a measure of external diameter 25. Standard needles range from 30 gauge which has an external diameter of 12/1000 of an inch to 6 gauge which has an external diameter of 200/1000 of an inch. The incremental change in diameter between gauges is not uniform. For example, 29 gauge has a diameter of 13/1000 of an inch, only 1/1000 more than 30 gauge. At the other end of the spectrum, 7 gauge has an outer diameter of 180/1000 of an inch, 20/1000 less than 6 gauge.

Although safety syringe 1 may be used with any size needle 11, needles in the middle of the standard needle range—24 to 18 gauge—are expected to be used most often. A 24 gauge needle has an external diameter of 22/1000 while 18 gauge is 50/1000. When needle 11 falls into this middle range, it is anticipated that sheath 17, or at least tip end 18, should have an external diameter 26 of not more than about 150% of external diameter 25 of needle 11. In this size range, it is anticipated that the external diameter 26 of sheath 17, or at least tip end 18, should preferably be between about 118% and about 125% of external diameter 25 of needle 11. With larger needles 11, such as 6 or 7 gauge, it is expected that sheath 17 or tip end 18 should have an external diameter 26 of not more than about 133% and preferably about 110% of external diameter 25 of needle 11. It should be appreciated that the construction and composition of sheath 17 may allow it to be made thinner than the ranges given above in furtherance of the goal of patient comfort. Similarly, different construction and composition may force sheath 17 to be thicker in order to satisfy the goal puncture resistance.

In a preferred embodiment, safety syringe 1 will comprise a means 27 for locking sheath 17 in covered position 20. This will prevent sheath 17 from slipping back into exposed position 21 and also prevent safety syringe 1 from being inadvertently reused. One preferred embodiment of locking means 27 comprises a locking housing 28 extending from needle end 3 of barrel 2. Locking housing 28 contains an internal surface 29. At least one pair of detents 30 and 31 extend from internal surface 29, inward and perpendicular to needle 11. Each detent 30 and 31 has a needle edge 32 and a barrel edge 33. First detent 30 is closest to barrel 2 while second detent 31 is furthest from barrel 2. Barrel edge 33 of first detent 30 is sloped away from barrel 2. Needle edge 32 of first detent 30 is substantially perpendicular to locking housing 28 as is barrel edge 33 of second detent 31.

Locking means 27 will further comprise at least one lip 34 that extends substantially perpendicularly from connector 23. When sheath 17 is in place over needle 11, lip 34 will extend away from needle 11. In exposed position 21, lip 34 and at least part of connector 23 will be within locking housing 28, and lip 34 will be between first detent 30 and barrel 2. Thus, when sheath 17 and connector 23 are advanced toward covered position 20, lip 34 will encounter barrel edge 33 of first detent 30. Because of the slope of barrel edge 33 of first detent 30, lip 34 will ride over first detent 30 and continue moving toward covered position 20.

Lip 34 will continue moving in the same direction until it encounters barrel edge 33 of second detent 31. Because this edge is perpendicular to internal surface 29, lip 34 will not pass over it. Similarly, needle edge 32 of first detent 30 will prevent lip 34 from retreating over it. Therefore, lip 34 will be locked between first detent 30 and second detent 31. Likewise, sheath 17 will be locked in place. In this embodiment, sheath 17 should reach covered position 20 at least by the time lip 34 clears first detent 30.

In operation, safety syringe 1 will either come prefilled or it will come empty. If it is empty, it will be filled in the same manner as a normal syringe, that is by inserting needle 11 into a vial of liquid medication and then withdrawing plunger 8 until the requisite amount of liquid is obtained. Once safety syringe 1 is full, any air trapped in the syringe must be expelled. This is done by pointing needle 11 up and depressing plunger 8 until a small amount of liquid is expelled from needle 11. At this point, safety syringe 1 is ready to be used.

The person administering the injection will sterilize the skin in the region that is to receive the injection. Needle 11 will then be inserted into the tissue. Preferably, needle 11 will be inserted far enough so that tip end 18 of sheath 17 is also inserted into the tissue. To avoid unnecessarily deep injections, the distance between exposed position 21 and covered position 20 should be minimized. In a preferred embodiment, this distance is about ⅛ of an inch. Plunger 8 will then be depressed until washer end 10 engages diaphragm 15. In order to prevent pockets of medication from forming between washer end 10 and diaphragm 15, the surfaces of washer end 10 and diaphragm 15 should preferably fit together.

When washer end 10 has met diaphragm 15, the injection is complete. However, the person administering the injection should continue to press on plunger 8. This will cause diaphragm 15 to move toward needle 11 which in turn will cause connector 23 and sheath 17 to move in the same direction. Sheath 17 will thus move into covered position 20 before needle 11 is removed from the patient. If locking means 27 are used, sheath 17 will also be locked in covered position 20 prior to removal from the patient.

It is anticipated that these and other uses and embodiments will be obvious to those skilled in the art and are intended to be covered by the scope of the following claims.

We claim:

1. A safety syringe comprising:

a substantially hollow barrel having a needle end, a plunger end, and an interior wall extending between said plunger end and said needle end, wherein said needle end, said plunger end and said interior wall define a fluid receiving cavity within said barrel;

a plunger extending from said fluid receiving cavity of said barrel, said plunger having a thumb end and a washer end, said washer end configured to create a substantially fluid tight seal between said washer end and said interior wall of said barrel, whereby operation of said plunger will vary the volume of said fluid receiving cavity;

a needle extending from said needle end of said barrel, said needle having a pointed end, a barrel end, and an external diameter; and a sheath circumferentially positioned about said needle, said sheath having a tip end, said tip end having an external diameter, said tip end sized to be hypodermically insertable with said needle, said sheath having a covered position and an exposed position, said sheath operatively connected to said plunger to enable said sheath to be transferred from said exposed position into said covered position by advancement of said plunger.

2. A safety syringe according to claim 1 wherein said tip end of said sheath has an external diameter of not more than about 150% of said external diameter of said needle.

3. A safety syringe according to claim 1 wherein said tip end of said sheath has an external diameter of not more than about 133% of said external diameter of said needle.

4. A safety syringe according to claim 1 wherein said tip end of said sheath has an external diameter that is between about 118% and about 125% of said external diameter of said needle.

5. A safety syringe according to claim 1 wherein said tip end of said sheath has an external diameter of about 110% of said external diameter of said needle.

6. A safety syringe according to claim 1, wherein the shortest cross-sectional dimension of said tip end is less than the longest cross-sectional dimension of a puncture wound createable by said needle during hypodermic injection.

7. A safety syringe according to claim 1, wherein the longest cross-sectional dimension of said tip end is less than the longest cross-sectional dimension of a puncture wound createable by said needle during hypodermic injection.

8. A safety syringe according to claim 1 further comprising a means for creating a substantially fluid tight seal between said barrel end of said needle and said interior wall and said needle end of said barrel.

9. A safety syringe according to claim 8 wherein said sealing means comprises a diaphragm slidably positioned over said barrel end of said needle, said diaphragm sized to engage said interior wall of said barrel, said diaphragm containing an aperture allowing fluid passage through said diaphragm.

10. A safety syringe according to claim 8 wherein said tip end of said sheath has an external diameter of not more than about 150% of said external diameter of said needle.

11. A safety syringe according to claim 8 wherein said tip end of said sheath has an external diameter of not more than about 133% of said external diameter of said needle.

12. A safety syringe according to claim 8 wherein said tip end of said sheath has an external diameter that is between about 118% and about 125% of said external diameter of said needle.

13. A safety syringe according to claim 8 wherein said tip end of said sheath has an external diameter of about 110% of said external diameter of said needle.

14. A safety syringe according to claim 8 wherein the shortest cross-sectional dimension of said tip end is less than the longest cross-sectional dimension of a puncture wound createable by said needle during hypodermic injection.

15. A safety syringe according to claim 8 wherein the longest cross-sectional dimension of said tip end is less than the longest cross-sectional dimension of a puncture wound createable by said needle during hypodermic injection.

16. A safety syringe according to claim 1 further comprising a means for locking said sheath in said covered position.

17. A safety syringe according to claim 16 wherein said tip end of said sheath has an external diameter of not more than about 150% of said external diameter of said needle.

18. A safety syringe according to claim 16 wherein said tip end of said sheath has an external diameter of not more than about 133% of said external diameter of said needle.

19. A safety syringe according to claim 16 wherein said tip end of said sheath has an external diameter that is between about 118% and about 125% of said external diameter of said needle.

20. A safety syringe according to claim 16 wherein said tip end of said sheath has an external diameter of about 110% of said external diameter of said needle.

21. A safety syringe according to claim 16 wherein the shortest cross-sectional dimension of said tip end is less than the longest cross-sectional dimension of a puncture wound createable by said needle during hypodermic injection.

22. A safety syringe according to claim 16 wherein the longest cross-sectional dimension of said tip end is less than the longest cross-sectional dimension of a puncture wound createable by said needle during hypodermic injection.

23. A safety syringe according to claim 1 wherein said needle is hollow.

24. A safety syringe according to claim 23 wherein said needle provides fluid passage into and out of said fluid receiving cavity.

25. A safety syringe according to claim 24 wherein said tip end of said sheath has an external diameter of not more than about 150% of said external diameter of said needle.

26. A safety syringe according to claim 24 wherein said tip end of said sheath has an external diameter of not more than about 133% of said external diameter of said needle.

27. A safety syringe according to claim 24 wherein said tip end of said sheath has an external diameter that is between about 118% and about 125% of said external diameter of said needle.

28. A safety syringe according to claim 24 wherein said tip end of said sheath has at an external diameter of about 110% of said external diameter of said needle.

29. A safety syringe according to claim 24 wherein the shortest cross-sectional dimension of said tip end is less than the longest cross-sectional dimension of a puncture wound createable by said needle during hypodermic injection.

30. A safety syringe according to claim 24 wherein the longest cross-sectional dimension of said tip end is less than the longest cross-sectional dimension of a puncture wound createable by said needle during hypodermic injection.

31. A safety syringe according to claim 24 further comprising a means for creating a substantially fluid tight seal between said barrel end of said needle and said interior wall and said needle end of said barrel.

32. A safety syringe according to claim 31 wherein said sealing means comprises a diaphragm slidably positioned over said barrel end of said needle, said diaphragm sized to engage said interior wall of said barrel, said diaphragm containing an aperture allowing fluid passage through said diaphragm.

33. A safety syringe according to claim 31 wherein said tip end of said sheath has an external diameter of not more than about 150% of said external diameter of said needle.

34. A safety syringe according to claim 31 wherein said tip end of said sheath has an external diameter of not more than about 133% of said external diameter of said needle.

35. A safety syringe according to claim 31 wherein said tip end of said sheath has an external diameter that is between about 118% and about 125% of said external diameter of said needle.

36. A safety syringe according to claim 31 wherein said tip end of said sheath has an external diameter of about 110% of said external diameter of said needle.

37. A safety syringe according to claim 31 wherein the shortest cross-sectional dimension of said tip end is less than the longest cross-sectional dimension of a puncture wound createable by said needle during hypodermic injection.

38. A safety syringe according to claim 31 wherein the longest cross-sectional dimension of said tip end is less than the longest cross-sectional dimension of a puncture wound createable by said needle during hypodermic injection.

* * * * *